(12) United States Patent
Shimaru

(10) Patent No.: US 11,819,646 B2
(45) Date of Patent: Nov. 21, 2023

(54) METHOD FOR PRODUCING BALLOON CATHETER AND APPARATUS FOR PRODUCING MEDICAL RESIN BALLOON

(71) Applicant: KANEKA CORPORATION, Osaka (JP)

(72) Inventor: Masayasu Shimaru, Settsu (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 17/772,566

(22) PCT Filed: Oct. 16, 2020

(86) PCT No.: PCT/JP2020/039115
§ 371 (c)(1),
(2) Date: Apr. 28, 2022

(87) PCT Pub. No.: WO2021/131263
PCT Pub. Date: Jul. 1, 2021

(65) Prior Publication Data
US 2023/0041442 A1    Feb. 9, 2023

(30) Foreign Application Priority Data
Dec. 26, 2019 (JP) ................................. 2019-237208

(51) Int. Cl.
*B29C 49/48* (2006.01)
*A61M 25/10* (2013.01)
(Continued)

(52) U.S. Cl.
CPC .... *A61M 25/1029* (2013.01); *A61M 25/1034* (2013.01); *B29C 49/4823* (2013.01);
(Continued)

(58) Field of Classification Search
CPC ............ B29C 39/38; B29C 2049/4853; A61M 25/1027
See application file for complete search history.

(56) References Cited

U.S. PATENT DOCUMENTS 6,572,813 B1 * 6/2003 Zhang ................. B29C 67/0014
264/903
7,264,458 B2 * 9/2007 Holman .............. B29C 49/6445
264/458
(Continued)

FOREIGN PATENT DOCUMENTS

JP          7-285169 A        10/1995
JP          H07285169 A  *   10/1995
(Continued)

OTHER PUBLICATIONS

International Search Report, issued in PCT/JP2020/039115, PCT/ISA/210, dated Dec. 1, 2020.

*Primary Examiner* — Cachet I Proctor
(74) *Attorney, Agent, or Firm* — Birch, Stewart, Kolasch & Birch, LLP

(57) ABSTRACT

Providing a method for producing a balloon catheter, that is capable of uniformly heating and cooling the entire mold and less likely to cause temperature unevenness. A method for producing a balloon catheter which comprises a shaft extending in a longitudinal direction and a medical resin balloon provided at a distal end portion of the shaft, comprising the steps of inserting a resin tubular body (10) into a mold (20), and placing the mold (20) inside a thermal jacket (30) wherein a porous metal body (50) is disposed outside the mold (20) and inside the thermal jacket (30).

22 Claims, 4 Drawing Sheets

(51) Int. Cl.
*B29C 49/64* (2006.01)
*B29L 31/00* (2006.01)

(52) U.S. Cl.
CPC ......... *B29C 49/64* (2013.01); *A61M 2207/10* (2013.01); *B29L 2031/7543* (2013.01)

(56) References Cited

U.S. PATENT DOCUMENTS

| | | | |
|---|---|---|---|
| 7,666,342 B2* | 2/2010 | Limon | B29B 13/024 |
| | | | 264/573 |
| 2003/0018387 A1 | 1/2003 | Schuessler | |
| 2004/0004308 A1 | 1/2004 | Schuessler | |
| 2004/0010225 A1 | 1/2004 | Schuessler | |
| 2006/0229712 A1* | 10/2006 | Wilson | A61F 2/958 |
| | | | 623/1.42 |
| 2008/0181981 A1 | 7/2008 | Schuessler | |
| 2008/0300670 A1* | 12/2008 | Gueriguian | A61F 2/91 |
| | | | 623/1.15 |
| 2009/0096134 A1* | 4/2009 | Holman | B29C 49/6445 |
| | | | 264/402 |

FOREIGN PATENT DOCUMENTS

| | | | | |
|---|---|---|---|---|
| JP | 2010-247538 A | 11/2010 | | |
| WO | WO-2015122101 A1 * | 8/2015 | | |
| WO | WO-2018180490 A1 * | 10/2018 | ............ | A61M 25/10 |

\* cited by examiner

[Fig. 1]
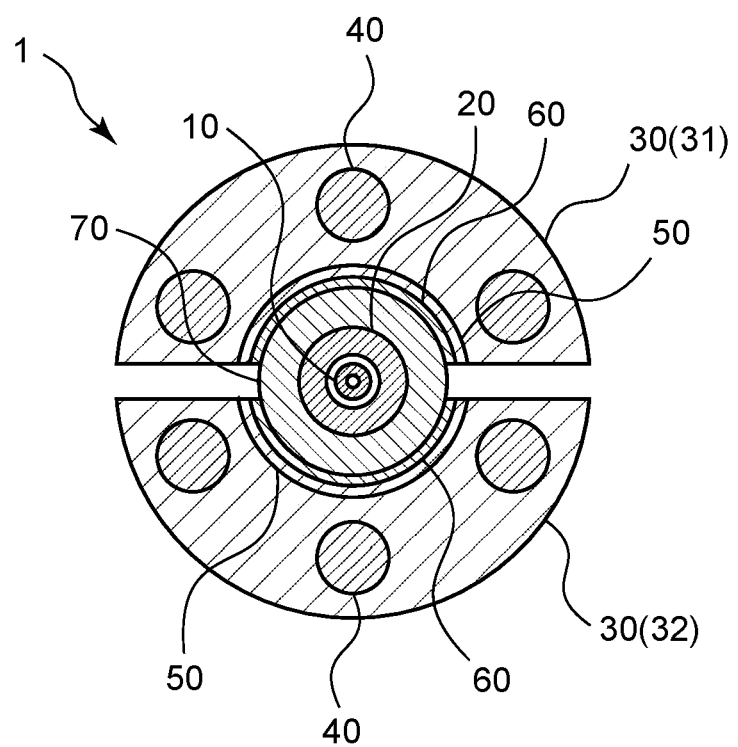

[Fig. 2]
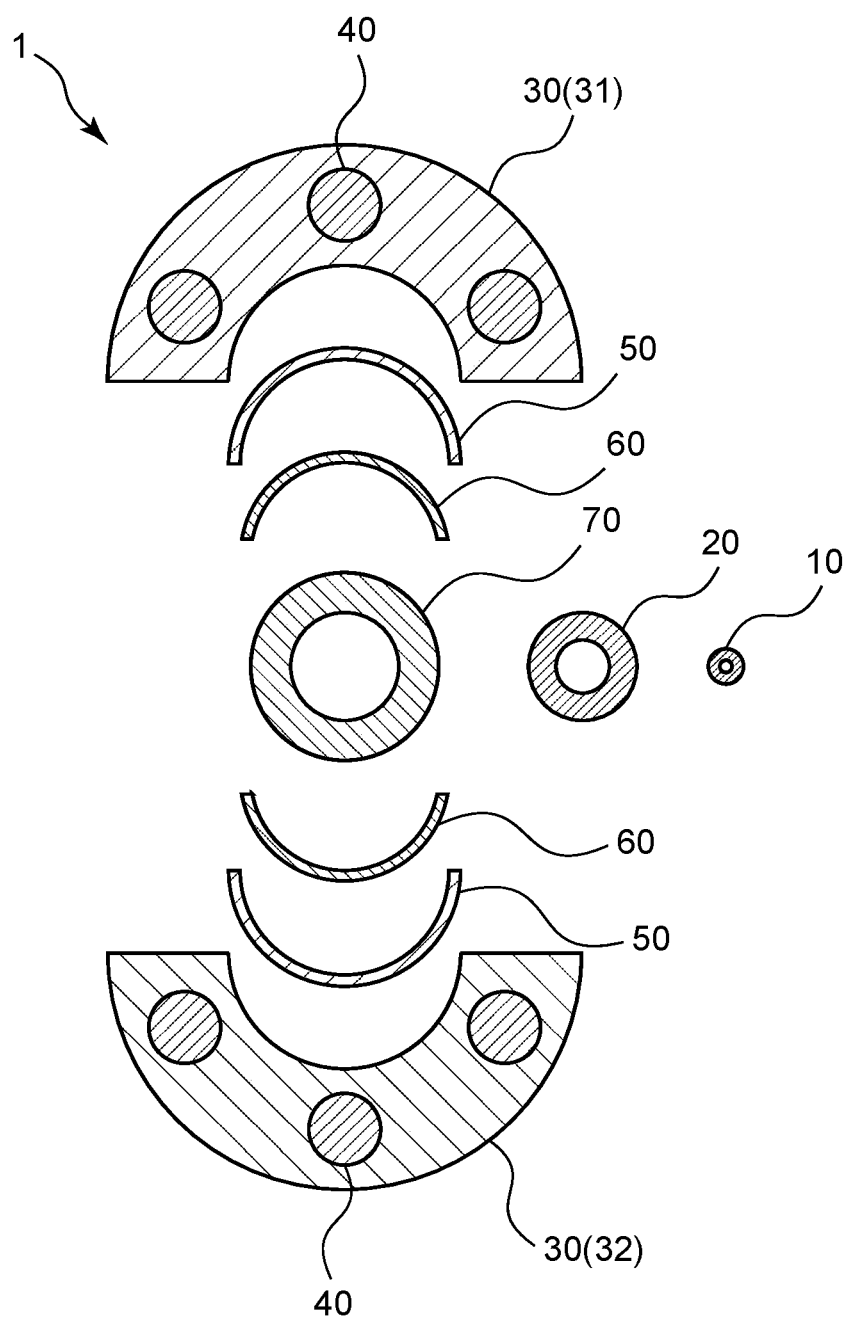

[Fig. 3]
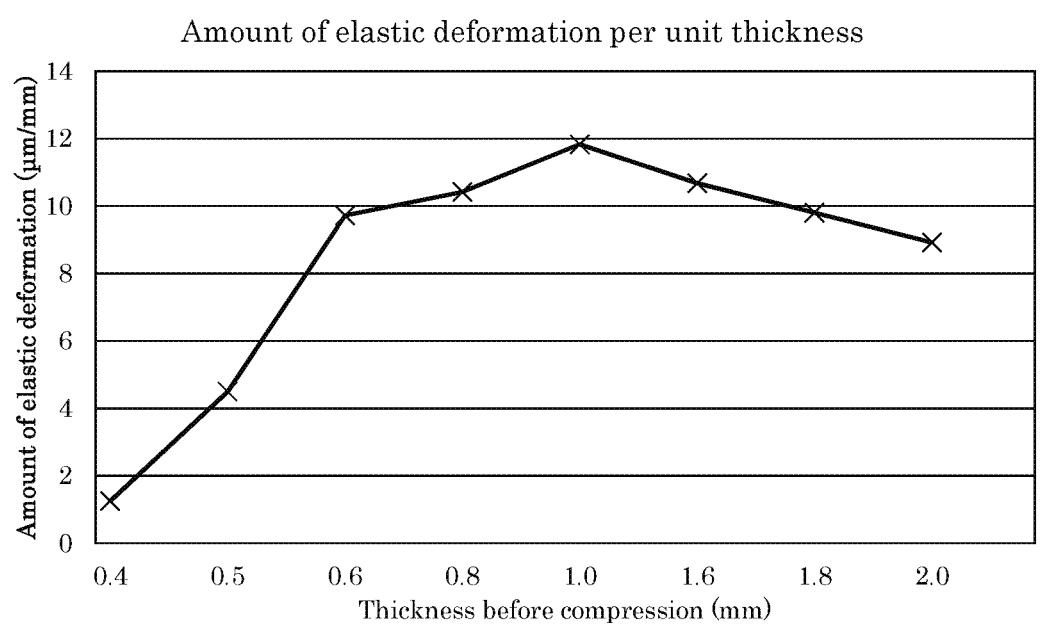

[Fig. 4]
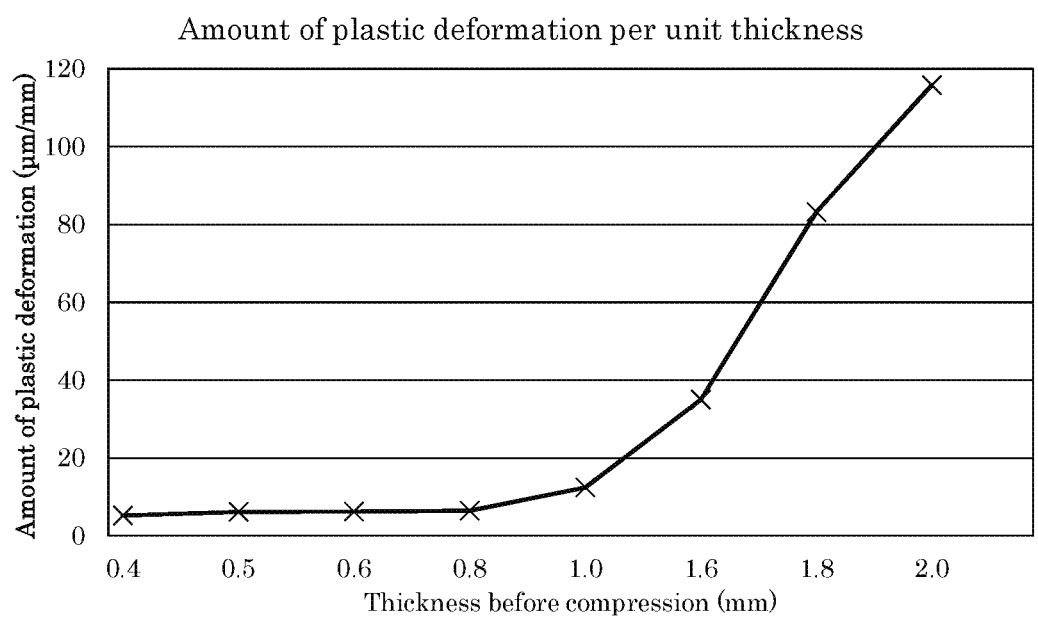

METHOD FOR PRODUCING BALLOON CATHETER AND APPARATUS FOR PRODUCING MEDICAL RESIN BALLOON

TECHNICAL FIELD

The present invention relates to a method for producing a balloon catheter having a medical balloon made of a resin and an apparatus for producing a medical balloon.

BACKGROUND ART

It is known that various diseases are caused due to stenosis of blood vessels, which is a flow path for blood circulation in a body, and congestion of blood circulation. In particular, stenosis of coronary arteries that supply blood to a heart can lead to serious diseases such as angina pectoris and myocardial infarction. As a method for treating such stenosis of blood vessels, there is a technique for dilating a stenotic part using a balloon catheter, such as angioplasty including PTA and PTCA. Angioplasty is a minimally invasive procedure that does not require thoracotomy such as bypass surgery, and is widely practiced.

As a method for producing a resin-made medical balloon used for a balloon catheter, for example, Patent Literature 1 describes a rotational molding system for molding a medical article, comprising a multi-axis rotational molding machine and a shaping mold mounted on the molding machine, wherein the interior of the shaping mold defines a cavity having a required shape of the medical article to be molded. Patent Literature 2 describes a resin shaping mold equipped with a mold temperature control mechanism, wherein the mold is made of porous sintered metal and has a non-permeable surface film made of metal, synthetic resin or ceramic on the cavity-facing surface, and the mold temperature control mechanism comprises a temperature control fluid supply pipe that supplies temperature control fluid to at least the mold and a temperature control fluid discharge pipe that discharges the temperature control fluid supplied to the mold from the mold.

CITATION LIST

Patent Literature

Patent Literature 1
Japanese Unexamined Laid-open Patent Application Publication No. 2010-247538
Patent Literature 2
Japanese Unexamined Laid-open Patent Application Publication No. 117-285169

SUMMARY OF INVENTION

Technical Problem

There was a problem that, if the balloon forming mold had uneven temperature when molding the balloon, thickness of the balloon might be uneven or the balloon might be bent in the length direction of the balloon. In a balloon produced by the molding system as in Patent Literature 1 or a balloon produced by using the shaping mold as in Patent Literature 2, it is difficult to heat and cool the balloon forming mold uniformly so that temperature unevenness may occur.

The present invention has been made in view of the above circumstances, and an object the present invention is to provide a method for producing a balloon catheter and an apparatus for producing a medical balloon made of a resin, those are capable of uniformly heating and cooling the entire mold and less likely to cause temperature unevenness.

Solution to Problem

A method for producing a balloon catheter, which solves the above problem, is a method for producing a balloon catheter which comprises a shaft extending in a longitudinal direction and a medical resin balloon provided at a distal end portion of the shaft, the method comprises the steps of inserting a resin tubular body into a mold, and placing the mold inside a thermal jacket wherein a porous metal body is disposed outside the mold and inside the thermal jacket.

In the method for producing a balloon catheter of the present invention, it is preferable that an amount of elastic deformation per unit thickness of the porous metal body is 3 μm/mm or more, and a thermal conductivity of the porous metal body is 0.325 W/m·K or more.

In the method for producing a balloon catheter of the present invention, it is preferable that an amount of initial plastic deformation per unit thickness of the porous metal body is 100 μm/mm or less.

In the method for producing a balloon catheter of the present invention, it is preferable that a metal content of material constituting the porous metal body is 90% or more.

In the method for producing a balloon catheter of the present invention, it is preferable that a number of pores per inch of the porous metal body is 8 ppi or more and 8500 ppi or less.

In the method for producing a balloon catheter of the present invention, it is preferable that the porous metal body contains at least one selected from the group consisting of gold, platinum, silver, copper, aluminum, stainless steel, titanium, molybdenum, tantalum, nickel and cobalt.

In the method for producing a balloon catheter of the present invention, it is preferable that the porous metal body is disposed on a part of the mold in an axial direction.

In the method for producing a balloon catheter of the present invention, it is preferable that a thin film member is disposed on an inside of the porous metal body.

In the method for producing a balloon catheter of the present invention, it is preferable that the thermal jacket includes a plurality of thermal jacket segments.

In the method for producing a balloon catheter of the present invention, it is preferable that the thermal jacket includes a first thermal jacket segment on one side of the mold and a second thermal jacket segment on the other side of the mold, and the first thermal jacket segment and the second thermal jacket segment are connected to each other.

In the method for producing a balloon catheter of the present invention, it is preferable that a housing member is disposed inside the thermal jacket and the mold is disposed inside the housing member.

An apparatus for producing a medical resin balloon, which solves the above problem, comprises a mold into which a resin tubular body is inserted, a thermal jacket inside which the mold is disposed, a porous metal body disposed outside the mold and inside the thermal jacket.

In the apparatus for producing a medical resin balloon of the present invention, it is preferable that an amount of elastic deformation per unit thickness of the porous metal body is 3 μm/mm or more, and a thermal conductivity of the porous metal body is 0.325 W/m·K or more.

In the apparatus for producing a medical resin balloon of the present invention, it is preferable that an amount of initial plastic deformation per unit thickness of the porous metal body is 100 μm/mm or less.

In the apparatus for producing a medical resin balloon of the present invention, it is preferable that a metal content of material constituting the porous metal body is 90% or more.

In the apparatus for producing a medical resin balloon of the present invention, it is preferable that a number of pores per inch of the porous metal body is 8 ppi or more and 8500 ppi or less.

In the apparatus for producing a medical resin balloon of the present invention, it is preferable that the porous metal body contains at least one selected from the group consisting of gold, platinum, silver, copper, aluminum, stainless steel, titanium, molybdenum, tantalum, nickel and cobalt.

In the apparatus for producing a medical resin balloon of the present invention, it is preferable that the porous metal body is disposed on a part of the mold in an axial direction.

In the apparatus for producing a medical resin balloon of the present invention, it is preferable that the apparatus further comprising a thin film member disposed on an inside of the porous metal body.

In the apparatus for producing a medical resin balloon of the present invention, it is preferable that the thermal jacket includes a plurality of thermal jacket segments.

In the apparatus for producing a medical resin balloon of the present invention, it is preferable that the thermal jacket includes a first thermal jacket segment on one side of the mold and a second thermal jacket segment on the other side of the mold, and the first thermal jacket segment and the second thermal jacket segment are connected to each other.

In the apparatus for producing a medical resin balloon of the present invention, it is preferable that a housing member is disposed inside the thermal jacket and the mold is disposed inside the housing member.

Advantageous Effects of Invention

According to the method for producing a balloon catheter of the present invention, since the method comprises the step of placing the mold inside the thermal jacket wherein the porous metal body is disposed outside the mold and inside the thermal jacket, the porous metal body can fill a gap between the thermal jacket and the mold. Therefore, the mold can be uniformly heated and cooled by the thermal jacket, and a balloon catheter having a balloon with less uneven thickness and less bending can be obtained.

According to the apparatus for producing a medical resin balloon of the present invention, since the apparatus comprises the thermal jacket inside which the mold is disposed and the porous metal body disposed outside the mold and inside the thermal jacket, the porous metal body fills a gap between the thermal jacket and the mold, and the mold can be uniformly heated or cooled by the thermal jacket Therefore, temperature unevenness of the mold is less likely to occur and it is possible to produce a balloon with less uneven thickness and less bending.

BRIEF DESCRIPTION OF DRAWINGS

FIG. 1 shows a cross-sectional view, perpendicular to a longitudinal direction of a resin tubular body, of an apparatus for producing a medical resin balloon according to an embodiment of the present invention.

FIG. 2 shows a schematic view of the apparatus for producing a medical resin balloon shown in FIG. 1 in a cross section perpendicular to the longitudinal direction of the resin tubular body.

FIG. 3 shows a graph of an amount of elastic deformation per unit thickness of a porous metal body according to an embodiment of the present invention.

FIG. 4 shows a graph of an amount of plastic deformation per unit thickness of a porous metal body according to an embodiment of the present invention.

DESCRIPTION OF EMBODIMENTS

Hereinafter, the present invention is specifically described below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching or a reference sign for a member may be omitted for convenience, and in such a case, the description and other drawings should be referred to. In addition, sizes of various members in the drawings may differ from the actual sizes thereof, since priority is given to understanding the features of the present invention.

FIG. 1 shows a cross-sectional view, perpendicular to a longitudinal direction of a resin tubular body 10, of a medical resin balloon production apparatus 1 according to an embodiment of the present invention, and FIG. 2 shows a schematic view of the medical resin balloon production apparatus 1 shown in FIG. 1 in a cross section perpendicular to the longitudinal direction of the resin tubular body 10. The longitudinal direction of the resin tubular body 10 can be rephrased as a distal and proximal direction of the resin tubular body 10.

A medical resin balloon in the present invention can be produced by applying pressure to the inside of the resin tubular body 10, heating the resin tubular body 10, and stretching it in the longitudinal direction. Specifically, the medical resin balloon can be produced by blow-molding the resin tubular body 10. In producing the medical resin balloon, the inside of the resin tubular body 10 may be pressurized before stretching, the inside of that may be pressurized at the same time as stretching, or the inside of that may be pressurized during or after stretching. Among them, it is preferable that the resin tubular body 10 is stretched in the longitudinal direction in the state where pressure is applied to the inside of the resin tubular body 10. As the medical resin balloon is produced by stretching the resin tubular body 10 in the longitudinal direction while pressure is applied to the inside of the resin tubular body 10, production efficiency of the medical resin balloon can be improved.

As shown in FIGS. 1 and 2, the medical resin balloon production apparatus 1 of the present invention is characterized to comprise a mold 20 into which the resin tubular body 10 is inserted, a thermal jacket 30 inside which the mold 20 is disposed, and a porous metal body 50 which is disposed outside the mold 20 and inside the thermal jacket 30. Hereinafter, the medical resin balloon production apparatus may be simply referred to as a "production apparatus". The production apparatus of the present invention can be also used for production of something other than a medical resin balloon.

The resin tubular body 10 is made of synthetic resin and is a so-called parison used for blow molding.

The material constituting the resin tubular body 10 is preferably a thermoplastic resin. Examples of the material constituting the resin tubular body 10 include polyolefin resins such as polyethylene, polypropylene, and an ethylenepropylene copolymer, polyester resins such as polyethylene terephthalate and polyester elastomer, polyurethane resins such as polyurethane and polyurethane elastomer, polyphenylene sulfide resins, polyamide resins such as polyamide and polyamide elastomer, vinyl chloride resins, silicone resins, and natural rubbers such as latex rubber. These may be used alone or in combination of two or more. Among them, a polyamide resin, a polyester resin, and a polyurethane resin are preferably used as the material constituting the resin tubular body 10. In particular, from the viewpoint of thinning and flexibility of the medical resin balloon, an elastomer resin is preferably used. For example, among polyamide resins, nylon 12, nylon 11 and the like are suitable materials for the resin tubular body 10, and nylon 12 is preferably used in view of being relatively easy to mold in blow molding. Further, from the viewpoint of thinning and flexibility of the medical resin balloon, polyamide elastomers such as a polyether ester amide elastomer and a polyamide ether elastomer are preferably used. Among them, a polyether ester amide elastomer is preferably used, since it has high yield strength and good dimensional stability of the medical resin balloon.

Thickness of the resin tubular body 10 can be set depending on the thickness of the medical resin balloon, and for example, it can be 3 mm or less, 2 mm or less, or 1 mm or less, and 0.05 mm or more, 0.07 mm or more, or 0.1 mm or more.

The resin tubular body 10 can be produced by, for example, extrusion molding, injection molding, or the like. Among them, the resin tubular body 10 is preferably produced by extrusion molding. As the resin tubular body 10 is produced by extrusion molding, it becomes possible to produce the resin tubular body 10 in large quantities in a short time, and production efficiency of the medical resin balloon can be improved.

The resin tubular body 10 is inserted to the inside of the mold 20, and the resin tubular body 10 is blow-molded, whereby the medical resin balloon is produced. The mold 20 has a space having the same shape as an outer shape of the medical resin balloon inside thereof, and the resin tubular body 10 is placed in the internal space.

The mold 20 is preferably composed of plurality segments of molds. Specifically, for example, the mold includes a center part mold which forms a straight tube portion of the middle of the medical resin balloon and end part molds which is arranged on both sides of the center part mold and form tapered portions located at both ends of the straight tube portion of the medical resin balloon. As the mold 20 includes the center part mold and the end part molds arranged on both sides of the center part mold, medical resin balloons having various shapes can be obtained by replacing the center part mold and the end part molds.

The material constituting the mold 20 is preferably a metal, and more preferably iron, copper, aluminum, or an alloy thereof. For example, examples of the iron alloy include stainless steel, examples of the copper alloy include brass, and examples of the aluminum alloy include duralumin. As the material constituting the mold 20 is iron, copper, aluminum, or an alloy thereof, heat capacity of the mold 20 is large and heat transfer of the mold 20 is high, so that temperature of the entire mold 20 tends to be uniform. As a result, temperature unevenness is less likely to occur in the resin tubular body 10 disposed inside the mold 20, thereby facilitating production of the medical resin balloon.

It is preferable that the length of the resin tubular body 10 in the longitudinal direction is longer than the length of the internal space of the mold 20 in the longitudinal direction. That is, it is preferable that both ends of the resin tubular body 10 are exposed from the mold 20 in the state where the resin tubular body 10 is disposed inside the mold 20. As the length of the resin tubular body 10 in the longitudinal direction is longer than the length of the internal space of the mold 20 in the longitudinal direction, the resin tubular body 10 can be easily blow-molded, and it becomes possible to increase the production efficiency of the medical resin balloon.

The length of the resin tubular body 10 in the longitudinal direction is preferably 1.05 times or more, more preferably 1.10 times or more, even more preferably 1.15 times or more of the length of the internal space of the mold 20. By setting the lower limit of the ratio of the length of the resin tubular body 10 in the longitudinal direction to the length of the internal space of the mold 20 in the above range, both ends of the resin tubular body 10 can be sufficiently grasped to allow the resin tubular body 10 to be stretched in both longitudinal directions during the blow molding of the resin tubular body 10, that easily performing start of the stretching step. The upper limit of the ratio of the length of the resin tubular body 10 in the longitudinal direction to the length of the internal space of the mold 20 can be, for example, 100 times or less, 90 times or less, 80 times or less, or 70 times or less of the length of the internal space of the mold 20.

The mold 20 is disposed inside the thermal jacket 30, which adjusts temperature of the mold 20. That is, the thermal jacket 30 can perform either or both heating and cooling of the mold 20.

As shown in FIGS. 1 and 2, the thermal jacket 30 is preferably provided with a temperature control member 40. In the case where the thermal jacket 30 is used for heating the mold 20, examples of the temperature control member 40 include a cartridge heater and others, and in the case where the thermal jacket 30 is used for cooling the mold 20, examples of the temperature control member 40 include a cooling water flow path and others. As the thermal jacket 30 is provided with the temperature control member 40, changing the temperature of the thermal jacket 30 is facilitated.

A porous metal body 50 is disposed outside the mold 20 and inside the thermal jacket 30. That is, the porous metal body 50 is disposed between the mold 20 and the thermal jacket 30.

The porous metal body 50 is a metal body having a plurality of pores. By arranging the porous metal body 50 on the outside of the mold 20 and the inside of the thermal jacket 30, pores of the porous metal body 50 sandwiched between the mold 20 and the thermal jacket 30 is collapsed, and the porous metal body 50 is deformed so that the porous metal body 50 can fill a gap existing between the mold 20 and the thermal jacket 30. As a result, temperature of the thermal jacket 30 can be easily transmitted to the mold 20 uniformly, and therefore, the thermal jacket 30 can uniformly heat or cool the mold 20, and it is possible to produce the medical resin balloon with less uneven thickness and less bending.

It is preferable that an amount of elastic deformation per unit thickness of the porous metal body 50 is 3 μm/mm or more, and a thermal conductivity of the porous metal body 50 is 0.325 W/m·K or more. As the amount of elastic deformation per unit thickness of the porous metal body 50 is 3 μm/mm or more and the thermal conductivity of the porous metal body 50 is 0.325 W/m·K or more, the porous metal body 50 comes to have both elastic deformability and thermal conductivity. Therefore, the porous metal body 50 can surely fill the gap between the mold 20 and the thermal jacket 30, and the temperature of the thermal jacket 30 can be surely transmitted to the mold 20, whereby the mold 20 is easily heated or cooled uniformly.

The amount of elastic deformation per unit thickness and the thermal conductivity of the porous metal body 50 are measured after the porous metal body 50 is compressed five times by applying a pressure of 100 N/cm$^2$ to the porous metal body 50 five times. This imitates a situation where the porous metal body 50 is repeatedly pressed against the mold 20, the thermal jacket 30 or the like using the production apparatus 1.

The amount of elastic deformation per unit thickness of the porous metal body 50 is preferably 3 μm/mm or more, more preferably 3.5 μm/mm or more, and even more preferably 4 μm/mm or more. By setting the lower limit of the amount of elastic deformation per unit thickness of the porous metal body 50 in the above range, the porous metal body 50 is easily elastically deformed, and the porous metal body 50 filled between the mold 20 and the thermal jacket 30 easily follows the shape of the gap. The upper limit of the amount of elastic deformation per unit thickness of the porous metal body 50 can be, for example, 30 μm/mm or less, 25 μm/mm or less, or 20 μm/mm or less.

The thermal conductivity of the porous metal body 50 is preferably 0.325 W/m·K or more, more preferably 0.412 W/m·K or more, and even more preferably 0.5 W/m·K or more. By setting the lower limit of the thermal conductivity of the porous metal body 50 in the above range, the porous metal body 50 has sufficient thermal conductivity in spite of having pores, the temperature of the thermal jacket 30 is easily transmitted to the mold 20, and it is possible to efficiently heat or cool the mold 20 by the thermal jacket 30. The upper limit of the thermal conductivity of the porous metal body 50 can be, for example, 400 W/m·K or less, 300 W/m·K or less, or 200 W/m·K or less.

The amount of initial plastic deformation per unit thickness of the porous metal body 50 is preferably 100 μm/mm or less. As the amount of initial plastic deformation per unit thickness of the porous metal body 50 is 100 μm/mm or less, large plastic deformation is unlikely to occur in the porous metal body 50 when placing the porous metal body 50 between the mold 20 and the thermal jacket 30, and it becomes possible to surely fill the porous metal body 50 in the gap between the mold 20 and the thermal jacket 30.

The amount of initial plastic deformation per unit thickness of the porous metal body 50 is preferably 100 μm/mm or less, more preferably 90 μm/mm or less, and even more preferably 85 μm/mm or less. By setting the upper limit of the amount of initial plastic deformation per unit thickness of the porous metal body 50 in the above range, the porous metal body 50 is less likely to be plastically deformed, and the porous metal body 50 is easily filled in the gap between the mold 20 and the thermal jacket 30 when placing the porous metal body 50 outside the mold 20 and inside the thermal jacket 30. The lower limit of the amount of initial plastic deformation per unit thickness of the porous metal body 50 can be, for example, 1 μm/mm or more, 3 μm/mm or more, or 5 μm/mm or more.

It is preferable that the metal content of the material constituting the porous metal body 50 is 90% or more. As the metal content of the material constituting the porous metal body 50 is 90% or more, strength of the porous metal body 50 is high, and it is possible to repeatedly place the porous metal body 50 outside the mold 20 and inside thermal jacket 30. Further, since it is possible to increase the thermal conductivity of the porous metal body 50, the temperature of the thermal jacket 30 can be efficiently transmitted to the mold 20, and the production efficiency of the medical resin balloon can be improved.

The metal content of the material constituting the porous metal body 50 is preferably 90% or more, more preferably 93% or more, and even more preferably 95% or more. By setting the lower limit of the metal content of the material constituting the porous metal body 50 in the above range, the strength and thermal conductivity of the porous metal body 50 can be increased. The metal content of the material constituting the porous metal body 50 is preferably higher, and the upper limit of the metal content can be, for example, 100% or less, 99.5% or less, or 99% or less.

It is preferable that a number of pores per inch of the porous metal body 50 is 8 ppi or more and 8500 ppi or less. As the number of pores per inch of the porous metal body 50 is 8 ppi or more and 8500 ppi or less, the porous metal body 50 is easily elastically deformed, and the gap existed between the mold 20 and the thermal jacket 30 is easily filled.

The number of pores per inch of the porous metal body 50 is preferably 8 ppi or more, more preferably 50 ppi or more, and even more preferably 100 ppi or more. By setting the lower limit of the number of pores per inch of the porous metal body 50 in the above range, elasticity of the porous metal body 50 can be increased. The number of pores per inch of the porous metal body 50 is preferably 8500 ppi or less, more preferably 8000 ppi or less, and even more preferably 7500 ppi. By setting the upper limit of the number of pores per inch of the porous metal body 50 in the above range, the temperature of the thermal jacket 30 is easily transmitted to the mold 20 while the porous metal body 50 has sufficient elasticity, and the production efficiency the medical resin balloon can be improved.

The porous metal body 50 preferably contains at least one selected from gold, platinum, silver, copper, aluminum, stainless steel, titanium, molybdenum, tantalum, nickel and cobalt. As the porous metal body 50 contains at least one selected from gold, platinum, silver, copper, aluminum, stainless steel, titanium, molybdenum, tantalum, nickel and cobalt, the porous metal body 50 can be made to have sufficient elasticity and thermal conductivity.

Among them, the porous metal body 50 more preferably contains at least one selected from silver, copper and nickel, and even more preferably contains silver. When the porous metal body 50 contains at least one selected from silver, copper and nickel, the porous metal body 50 is easily prepared, handling of that is facilitated, and the porous metal body 50 is made to have a good balance between elasticity and thermal conductivity.

The porous metal body 50 may be disposed on the entire axial direction of the mold 20, however, it is preferable that the porous metal body 50 is disposed on a part of the mold 20 in the axial direction. As the porous metal body 50 is disposed on a part of the mold 20 in the axial direction, a portion where the mold 20 and the thermal jacket 30 are in contact with each other via the porous metal body 50 and there is no gap between the mold 20 and the thermal jacket 30 can be provided in the axial direction of the mold 20. The temperature of the thermal jacket 30 can be transmitted to the mold 20 from the portion where the mold 20 and the thermal jacket 30 are in contact with each other via the porous metal body 50, and the thermal jacket 30 can be uniformly heated or cooled.

Although it not shown in the drawings, it is preferable that the porous metal body 50 is also disposed between the thermal jacket 30 and the temperature control member 40.

As the porous metal body 50 is disposed between the thermal jacket 30 and the temperature control member 40, the porous metal body 50 can fill a gap between the thermal jacket 30 and the temperature control member 40. Therefore, temperature of the temperature control member 40 is easily transmitted to the thermal jacket 30, and heat diffusion ability of the porous metal body 50 is high in the surface direction, so that the temperature of the thermal jacket 30 can be made uniform rapidly.

As shown in FIG. 1, it is preferable that the production apparatus 1 comprises a thin film member 60 disposed on the inside of the porous metal body 50. That is, it is preferable that the thin film member 60 is disposed inside the porous metal body 50 and outside the mold 20. When the production apparatus 1 comprises the thin film member 60, the thin film member 60 can protect a surface of the porous metal body 50. Therefore, even when the mold 20 is detached from the thermal jacket 30 and the porous metal body 50 in repeatedly using the production apparatus 1, the thin film member 60 protects the surface of the porous metal body 50, and the porous metal body 50 is prevented from being damaged.

Examples of the material constituting the thin film member 60 include metals such as silver, copper, iron, nickel and an alloy thereof, synthetic resins such as an aromatic polyetherketone resin (e.g., polyetheretherketone (PEEK)), a polyimide resin and a fluororesin (e.g., ethylene-tetrafluoroethylene copolymer (ETFE)), and others. Among them, the material constituting the thin film member 60 is preferably a metal, and more preferably the same material as the material constituting the porous metal body 50. As the material constituting the thin film member 60 is a metal, thermal conductivity of the thin film member 60 is increased, and the thin film member 60 is less likely to interfere with heat conduction in transmitting the temperature of the thermal jacket 30 to the mold 20 via the porous metal body 50 and the thin film member 60.

It is preferable that the size of the thin film member 60 is larger than the size of the porous metal body 50. As the size of the thin film member 60 is larger than the size of the porous metal body 50, the thin film member 60 can sufficiently protect the surface of the porous metal body 50, and the porous metal body 50 can be less likely to be damaged.

It is preferable that the thickness of the thin film member 60 is thinner than the thickness of the porous metal body 50. As the thickness of the thin film member 60 is thinner than the thickness of the porous metal body 50, the thin film member 60 is easily deformed along the shape of a member in contact with the thin film member 60 such as the mold 20, and the thin film member 60 can be brought into close contact with the member such as the mold 20. As a result, the temperature of the thermal jacket 30 can be easily transmitted to the member such as the mold 20 via the thin film member 60.

In heating the mold 20, the temperature of the thermal jacket 30 is preferably equal to or higher than the heating target temperature of the mold 20, and in cooling the mold 20, the temperature of the thermal jacket 30 is preferably equal to or lower than the cooling target temperature of the mold 20.

In heating the mold 20, the lower limit of the temperature of the thermal jacket 30 is preferably 1° C. higher, more preferably 5° C. higher, even more preferably 10° C. higher, still even more preferably 15° C. higher, particularly preferably 20° C. higher than the heating target temperature of the mold 20. By setting the lower limit of the temperature of the thermal jacket 30 in the above range, the temperature of the mold 20 can be raised to the heating target temperature in a short time. The upper limit of the temperature of the thermal jacket 30 in heating the mold 20 is preferably 250° C. higher, more preferably 225° C. higher, even more preferably 200° C. higher than the heating target temperature of the mold 20. By setting the upper limit of the temperature of the thermal jacket 30 in the above range, the temperature of the mold 20 can be easily adjusted.

In cooling the mold 20, the upper limit of the temperature of the thermal jacket 30 is preferably 1° C. lower, more preferably 3° C. lower, even more preferably 5° C. lower, still even more preferably 7° C. lower, particularly preferably 10° C. lower than the cooling target temperature of the mold 20. By setting the upper limit of the temperature of the thermal jacket 30 in the above range, the temperature of the mold 20 can be rapidly lowered to the cooling target temperature. The lower limit of the temperature of the thermal jacket 30 in cooling the mold 20 is preferably 100° C. lower, more preferably 90° C. lower, even more preferably 80° C. lower than the cooling target temperature of the mold 20. By setting the lower limit of the temperature of the thermal jacket 30 in the above range, the temperature of the mold 20 can be easily adjusted.

It is preferable that the thermal jacket 30 includes a heating jacket used for heating the mold 20 and a cooling jacket used for cooling the mold 20. When the thermal jacket 30 includes both a heating jacket and a cooling jacket, the temperature of the thermal jacket 30 does not need to be changed significantly in producing the resin medical balloon, such as changing the temperature of the thermal jacket 30 from a temperature suitable for heating the mold 20 to a temperature suitable for cooling the mold 20, and the time required for temperature adjustment of the thermal jacket 30 can be reduced. As a result, it is possible to improve the production efficiency of the medical resin balloon.

It is preferable that the thermal jacket 30 includes a plurality of thermal jacket segments. That is, the thermal jacket 30 is preferably composed of a plurality of thermal jacket segments. As the thermal jacket 30 includes a plurality of thermal jacket segments, the thermal jacket 30 can be divided, and it is facilitated to place the mold 20 and the porous metal body 50 inside the thermal jacket 30.

The plurality of thermal jacket segments may be arranged in the circumferential direction of the mold 20 or may be arranged in the axial direction of the mold 20. In the case where the plurality of thermal jacket segments are arranged in the circumferential direction of the mold 20, for example, the thermal jacket 30 can be made into a half-divided structure, and it is facilitated to place the mold 20 and the porous metal body 50 inside the thermal jacket 30. In the case where the plurality of thermal jacket segments are arranged in the axial direction of the mold 20, the temperature of each thermal jacket segment can be set independently, and it is possible to vary the heating or cooling temperature of the mold 20 in the axial direction of the mold 20.

As shown in FIGS. 1 and 2, it is preferable that the thermal jacket 30 includes a first thermal jacket segment 31 on one side of the mold 20 and a second thermal jacket segment 32 on the other side of the mold 20, and the first thermal jacket segment 31 and the second thermal jacket segment 32 are connected to each other. As the first thermal jacket segment 31 and the second thermal jacket segment 32 are connected to each other, the thermal jacket 30 has a structure that can be opened and closed on one side and the other side of the mold 20. As a result, it becomes easy to place or remove the mold 20 inside the thermal jacket 30, and the production efficiency of the medical resin balloon can be improved.

As a method of connecting the first thermal jacket segment 31 and the second thermal jacket segment 32 to each other, for example, a method such that the first thermal jacket segment 31 and the second thermal jacket segment 32 are connected via a cylinder or via a hinge is mentioned. Among them, it is preferable that the first thermal jacket segment 31 and the second thermal jacket segment 32 are connected to each other via a cylinder. As the first thermal jacket segment 31 and the second thermal jacket segment 32 are connected to each other via a cylinder, the thermal jacket 30 can be opened and closed by the cylinder, and the opening and closing operation of the thermal jacket 30 is facilitated and becomes reliable. Further, by connecting the first thermal jacket segment 31 and the second thermal jacket segment 32 to each other via the cylinder, it becomes possible to control the force that presses the first thermal jacket segment 31 and the second thermal jacket segment 32 against an inclusion such as a mold 20. Examples of types of the cylinder include, for example, an air cylinder, a hydraulic cylinder, an electric cylinder, and others.

It is preferable that a housing member 70 is disposed inside the thermal jacket 30, and inside the housing member 70, the mold 20 is disposed. That is, it is preferable that the housing member 70 is disposed outside the mold 20 and the thermal jacket 30 is disposed outside the housing member 70. As the housing member 70 is disposed inside the thermal jacket 30, the mold 20 can be easily handled in the case where the mold 20 is small or in the case where the mold 20 includes plurality segments of molds, whereby the production efficiency of the medical resin balloon can be improved.

In the case where the housing member 70 is disposed inside the thermal jacket 30, it is preferable that the porous metal body 50 is disposed inside the thermal jacket 30 and outside the housing member 70. That is, it is preferable that the porous metal body 50 is disposed between the thermal jacket 30 and the housing member 70. As the porous metal body 50 is disposed inside the thermal jacket 30 and outside the housing member 70, the porous metal body 50 fills a gap between the thermal jacket 30 and the housing member 70, and the temperature of the thermal jacket 30 can be uniformly transmitted to the housing member 70. As a result, the mold 20 can be also uniformly heated or cooled via the housing member 70.

Examples of the material constituting the housing member 70 include, for example, metals such as iron, copper, aluminum and an alloy thereof, synthetic resins such as an aromatic polyetherketone resin (e.g., polyetheretherketone (PEEK)), a polyimide resin and a fluororesin (e.g., ethylene-tetrafluoroethylene copolymer (ETFE)), and others. Among them, the material constituting the housing member 70 is preferably a metal, and more preferably the same metal as the metal constituting the mold 20. As the material constituting the housing member 70 is a metal, the temperature of the thermal jacket 30 is easily transmitted to the housing member 70, and it becomes easy to uniformly transmit the temperature of the thermal jacket 30 to the mold 20 via the housing member 70.

A method for producing a balloon catheter of the present invention is explained. In the following description, the part that overlaps with the above description is omitted.

The method for producing a balloon catheter of the present invention is a method for producing a balloon catheter which comprises a shaft extending in a longitudinal direction and a medical resin balloon provided at a distal end part of the shaft, the method being characterized to comprise the steps of inserting a resin tubular body into a mold, and placing the mold inside a thermal jacket wherein a porous metal body is disposed outside the mold and inside the thermal jacket. Hereinafter, the medical resin balloon may be simply referred to as a "balloon".

In the present invention, a distal side refers to a direction on a treatment target (an affected part) side with respect to an extending direction of the balloon, and a proximal side refers to an opposite side of the distal side, that is, a direction on a user's hand (i.e., a surgeon's hand) side with respect to the extending direction of the balloon. Further, the direction from the proximal side to the distal side of the balloon is referred to as a longitudinal direction.

The balloon catheter is configured so that fluid is supplied to the inside of the balloon through the shaft, and expansion and contraction of the balloon can be controlled using an indeflator (balloon pressurizer). The fluid may be a pressure fluid pressurized by a pump or the like.

The shaft extends in a distal and proximal direction and has a fluid flow channel inside thereof. The shaft also preferably has a guide wire insertion channel inside thereof. Examples of a configuration of which the shaft has the fluid flow channel and the guide wire insertion channel inside thereof includes, for example, a configuration of which the shaft comprises an outer tube and an inner tube. With such a configuration of the shaft, the inner tube can function as the guide wire insertion channel, and the space between the inner tube and the outer tube can function as the fluid flow channel. In the case where the shaft comprises the outer tube and the inner tube, it is preferable that the inner tube extends from a distal end of the outer tube and penetrates the balloon in the distal and proximal direction, a distal part of the balloon is joined to the inner tube, and a proximal part of the balloon is joined to the outer tube.

The present invention can be applied to both a so-called over-the-wire type balloon catheter, in which a wire is inserted from a distal part of the shaft to a proximal part of the shaft, and a so-called rapid-exchange type balloon catheter, in which a wire is inserted from a distal part of the shaft to the middle of a proximal part of the shaft. In the case where the balloon catheter is the over-the-wire type one, a hub may provided on the proximal side of the shaft for feeding fluid into the shaft, although it is not shown in the drawings. The hub preferably has a fluid injection part that is connected to the fluid flow channel through which fluid is supplied to the inside of the balloon. The balloon catheter having the hub with the fluid injection part facilitates the operation of expansion and contraction of the balloon by supplying fluid to the inside of the balloon. In the case where the balloon catheter is the over-the-wire type one, it is preferable that a guide wire insertion part that is connected to the guide wire insertion channel is provided. As the over-the-wire type balloon catheter comprises the hub with the guide wire insertion part, the operation of delivering the balloon catheter along the guide wire to a treatment target site is facilitated.

Joining of the shaft to the hub can be performed, for example, by bonding with an adhesive, welding, or the like. Among them, the shaft and the hub are preferably joined to each other by bonding. By bonding the shaft and hub to each other, joining strength between the shaft and hub is increased and durability of the balloon is improved, even when the shaft and hub are made of different materials to each other, for example in the case where the shaft is made of a flexible material and the hub is made of a rigid material.

Examples of the material constituting the shaft include, for example, a polyamide resin, a polyester resin, a polyurethane resin, a polyolefin resin, a fluororesin, a vinyl chloride resin, a silicone resin, a natural rubber and others. These may be used alone or in combination of two or more. Among them, the material constituting the shaft is preferably at least one selected from a polyamide resin, a polyolefin resin and a fluororesin. When the material constituting the shaft is at least one selected from a polyamide resin, a polyolefin resin and a fluororesin, slipperiness of the surface of the shaft can be increased and insertability of the balloon catheter into a blood vessel can be improved.

The balloon is provided on a distal end part of the shaft. Examples of joining means between the balloon and the shaft includes, for example, bonding with an adhesive, welding, caulking by attaching a ring member to a portion where the balloon and the shaft overlap, and others. Among them, the balloon and the shaft are preferably joined to each other by welding. By welding the balloon and the shaft together, joining strength between the balloon and the shaft can be increased, and the joint between the balloon and the shaft is less likely to be broken even when the balloon is repeatedly expanded and contracted.

The balloon preferably has a straight tube portion, a proximal tapered portion connected to a proximal side of the straight tube portion, and a distal tapered portion connected to a distal side of the straight tube portion. The proximal tapered portion and the distal tapered portion are preferably formed so as to reduce the diameter as being away from the straight tube portion. As the balloon has the straight tube portion, the straight tube portion is sufficiently in contact with stenosis, that makes easier to dilate the stenosis. Further, as the balloon has the proximal tapered portion and the distal tapered portion whose outer diameters decrease as being away from the straight tube portion, the outer diameter of distal and proximal end parts of the balloon can be reduced when the balloon is deflated and wrapped around the shaft, whereby the step between the shaft and the balloon is reduced, that facilitates insertion of the balloon in the longitudinal direction. In the present invention, an expansionable portion is considered to be the balloon.

The outer diameter of the balloon is preferably 0.5 mm or larger, more preferably 1 mm or larger, and even more preferably 1.5 mm or larger. By setting the lower limit of the outer diameter of the balloon in the above range, stenosis in a blood vessel can be sufficiently dilated. The outer diameter of the balloon is preferably 35 mm or smaller, more preferably 30 mm or smaller, and even more preferably 25 mm or smaller. By setting the upper limit of the outer diameter of the balloon in the above range, it is possible to prevent the outer diameter of the balloon from becoming large.

The length of the balloon in the longitudinal direction is preferably 5 mm or longer, more preferably 10 mm or longer, and even more preferably 15 mm or longer. By setting the lower limit of the length of the balloon in the longitudinal direction in the above range, it is possible to dilate a large area of stenosis at one time, thereby shortening the time required for the procedure. The length of the balloon in the longitudinal direction is preferably 300 mm or shorter, more preferably 200 mm or shorter, and even more preferably 100 mm or shorter. By setting the upper limit of the longitudinal length of the balloon in the above range, the amount of fluid supplied to the inside of the balloon for dilation of stenosis is reduced, thereby shortening the time required for the balloon to be fully inflated.

The thickness of the balloon is preferably 5 μm or more, more preferably 7 μm or more, and even more preferably 10 μm or more. By setting the lower limit of the thickness of the balloon in the above range, strength of the balloon can be increased and stenosis can be sufficiently dilated. The upper limit of the thickness of the balloon can be set depending on the application of the balloon catheter, and can be, for example, 100 μm or less, 90 μm or less, or 80 μm or less.

The method for producing a balloon catheter of the present invention comprises a step of inserting a resin tubular body into a mold and a step of placing the mold inside a thermal jacket.

The mold has an internal space that has the same shape as the outer shape of the medical resin balloon. In the step of inserting the resin tubular body into the mold, the resin tubular body is placed in the internal space of the mold. After the step of inserting the resin tubular body into the mold, the resin tubular body is blow-molded to produce a balloon.

The thermal jacket has a structure that the mold can be placed inside and adjust temperature of the mold disposed inside thereof. In the step of placing the mold inside the thermal jacket, at least one of heating and cooling of the mold by the thermal jacket is conducted.

As a specific example, in the case where heating of the mold by the thermal jacket is conducted, the resin tubular body may be blow-molded after the mold is heated by the thermal jacket. In the case where cooling of the mold by the thermal jacket is conducted, after the resin tubular body is blow-molded, the mold may be cooled by the thermal jacket to cool the molded balloon.

The porous metal body is disposed outside the mold and inside the thermal jacket. That is, the porous metal body is disposed between the mold and the thermal jacket. By arranging the porous metal body outside the mold and inside the thermal jacket, pores of the porous metal body sandwiched between the mold and the thermal jacket is collapsed, and the porous metal body is deformed so that the porous metal body can fill a gap existing between the mold and the thermal jacket. Therefore, temperature of the thermal jacket is easily transmitted to the mold uniformly, and the mold can be uniformly heated or cooled by the thermal jacket. As a result, uneven thickness and bending of the balloon are less likely to occur.

As described above, the apparatus for producing a medical resin balloon of the present invention is characterized to comprise a mold into which a resin tubular body is inserted, a thermal jacket inside which the mold is disposed, and a porous metal body disposed outside the mold and inside the thermal jacket. Further, the method for producing a balloon catheter of the present invention, where the balloon catheter comprises a shaft extending in a longitudinal direction and a medical resin balloon provided at a distal end part of the shaft, is characterized to comprise the steps of inserting a resin tubular body into a mold and placing the mold inside a thermal jacket wherein a porous metal body is disposed outside the mold and inside the thermal jacket. According to the apparatus for producing a medical resin balloon and the method for producing a balloon catheter of the present invention, since the thermal jacket inside which the mold is disposed is provided and the porous metal body is disposed outside the mold and the inside the thermal jacket, the porous metal body fills the gap between the thermal jacket and the mold, the mold can be uniformly heated or cooled by the thermal jacket, and therefore, temperature unevenness is less likely to occur and it is possible to produce a balloon with less uneven thickness and less bending.

This application claims priority to Japanese Patent Application No. 2019-237208, filed on Dec. 26, 2019. All of the contents of the Japanese Patent Application No. 2019-237208, filed on Dec. 26, 2019, are incorporated by reference herein.

EXAMPLES

Hereinafter, the present invention is described in more detail with reference to example; however, the present invention is not restricted by the examples described below of course, and can be certainly put into practice after appropriate modifications within in a range meeting the gist of the above and the below, all of which are included in the technical scope of the present invention.

(Density and Foaming Ratio of Porous Metal Body Before Compression)

As a porous metal body, a silver test piece (rectangular shape of 5 mm×25 mm) containing pores was prepared, and the density was determined by measuring the mass. A foaming ratio of the porous metal body was calculated from the ratio of the calculated density of the porous metal body to the density of the material constituting the porous metal body. The results are shown in Table 1. The density and foaming ratio of the porous metal body were measured without performing the compression operation described below.

Foaming ratio=density of material constituting test piece/density of test piece

Calculating the foaming ratio of the porous metal body is explained with reference to the test piece 1 (silver, thickness before compression: 0.4 mm) shown in Table 1 as a specific example. The density of the Test piece 1 is 3.75 g/cm$^3$, and the density of silver, which is a metal constituting the test piece 1, is 10.5 g/cm$^3$. From the density of the material constituting the test piece/the density of the test piece=10.5 (g/cm$^3$)/3.75 (g/cm$^3$), the foaming ratio of the test piece 1 is calculated to be 2.8 times.

(Amount of Elastic Deformation Per Unit Thickness of Porous Metal Body)

As a porous metal body, a silver test piece (rectangular shape of 5 mm×25 mm) containing pores was prepared, and the thickness was measured. The measured value of this thickness is taken as thickness of the test piece before compression.

Next, the operation of compressing the test piece by applying a pressure of 100 N/cm$^2$ (0.5 MPa) to the test piece was repeated 5 times, and the thickness of the test piece while applying a pressure of 0.5 MPa was measured. This operation imitates a situation where the porous metal body is repeatedly pressed against the mold, the thermal jacket, or the like using the medical resin balloon production apparatus. The measured value of this thickness is taken as thickness of the test piece during compression.

Then, the thickness of the test piece was measured while applying a pressure of 0.1 MPa to the test piece after repeating the operation of applying a pressure of 0.5 MPa to compress 5 times. This operation is to eliminate the influence of measurement error due to wobble on the surface of the porous metal body when measuring the thickness of the test piece. That is, in order to eliminate the influence of the surface property of the test piece, the thickness of the test piece under a pressure of 0.1 MPa is used as a reference. The measured value of this thickness is taken as thickness of the test piece after compression.

The value obtained by subtracting the thickness of the test piece during compression from the thickness of the test piece after compression was determined as an amount of elastic deformation. The amount of elastic deformation divided by the thickness of the test piece before compression was calculated as the "amount of elastic deformation per unit thickness". The results are shown in Table 1 and FIG. 3, which is a graph showing the amount of elastic deformation per unit thickness of the porous metal body.

Amount of elastic deformation per unit thickness=(thickness of test piece after compression−thickness of test piece during compression)/thickness of test piece before compression (Amount of Plastic Deformation Per Unit Thickness of Porous Metal Body)

The value obtained by subtracting the thickness after compression from the thickness of the test piece before compression described above was referred to as an amount of plastic deformation. The amount of plastic deformation divided by the thickness of the test piece before compression was calculated as the "amount of plastic deformation per unit thickness". The results are shown in Table 1 and FIG. 4, which is a graph showing the amount of plastic deformation per unit thickness of the porous metal body.

Amount of plastic deformation per unit thickness=(thickness of test piece before compression−thickness of test piece after compression)/thickness of test piece before compression

TABLE 1

| | Density before compression (g/cm$^3$) | Foaming ratio before compression (times) | Thickness of test piece (mm) | | |
|---|---|---|---|---|---|
| | | | Before compression | During compression (0.5 MPa) | After compression (0.1 MPa) |
| 1 | 3.75 | 2.8 | 0.4 | 0.397 | 0.398 |
| 2 | 3.04 | 3.5 | 0.5 | 0.495 | 0.497 |
| 3 | 2.33 | 4.5 | 0.6 | 0.590 | 0.596 |
| 4 | 2.02 | 5.2 | 0.8 | 0.787 | 0.795 |
| 5 | 1.52 | 6.9 | 1.0 | 0.976 | 0.988 |
| 6 | 1.08 | 9.7 | 1.6 | 1.527 | 1.544 |
| 7 | 0.96 | 10.9 | 1.8 | 1.633 | 1.650 |
| 8 | 0.95 | 11.0 | 2.0 | 1.751 | 1.768 |

TABLE 1-continued

|   | Amount of elastic deformation (μm) | Amount of elastic deformation per unit thickness (μm/mm) | Amount of plastic deformation (μm) | Amount of plastic deformation per unit thickness (μm/mm) |
|---|---|---|---|---|
| 1 | 0.50 | 1.25 | 2.08 | 5.21 |
| 2 | 2.25 | 4.50 | 3.09 | 6.17 |
| 3 | 5.83 | 9.72 | 3.75 | 6.25 |
| 4 | 8.33 | 10.42 | 5.17 | 6.46 |
| 5 | 11.83 | 11.83 | 12.42 | 12.42 |
| 6 | 17.08 | 10.68 | 55.92 | 34.95 |
| 7 | 17.67 | 9.80 | 149.74 | 83.19 |
| 8 | 17.83 | 8.92 | 231.66 | 115.83 |

A porous metal body of which the amount of elastic deformation per unit thickness is 3 μm/mm or more can be sufficiently deformed along unevenness of the mold and the thermal jacket. Therefore, heat of the thermal jacket can be uniformly transmitted to the mold, that is preferable. Further, a porous metal body of which the amount of plastic deformation per unit thickness is 100 μm/mm or less is less likely to leave dents and more likely to return to the original shape after being deformed along the mold and the thermal jacket and then removed from the mold and thermal jacket. Therefore, even when the porous metal body is repeatedly used, the gap between the porous metal body and the mold or the thermal jacket is less likely to occur, and the mold can be uniformly heated and cooled, that is preferable.

REFERENCE SIGNS LIST

1: medical resin balloon production apparatus
10: resin tubular body
20: mold
30: thermal jacket
31: first thermal jacket segment
32: second thermal jacket segment
40: temperature control member
50: porous metal body
60: thin film member
70: housing member

The invention claimed is:

1. A method for producing a balloon catheter which comprises a shaft extending in a longitudinal direction and a medical resin balloon provided at a distal end portion of the shaft, comprising the steps of:
   inserting a resin tubular body into a mold; and
   placing the mold inside a thermal jacket, so that a porous metal body is disposed outside the mold and inside the thermal jacket to fill a gap that exists between the mold and the thermal jacket, so as to produce the balloon catheter from the resin tubular body.

2. The method for producing a balloon catheter according to claim 1, wherein
   an amount of elastic deformation per unit thickness of the porous metal body is 3 μm/mm or more, and
   a thermal conductivity of the porous metal body is 0.325 W/m·K or more.

3. The method for producing a balloon catheter according to claim 1, wherein
   an amount of initial plastic deformation per unit thickness of the porous metal body is 100 μm/mm or less.

4. The method for producing a balloon catheter according to claim 1, wherein
   a metal content of material constituting the porous metal body is 90% or more.

5. The method for producing a balloon catheter according to claim 1, wherein
   a number of pores per inch of the porous metal body is 8 ppi or more and 8500 ppi or less.

6. The method for producing a balloon catheter according to claim 1, wherein
   the porous metal body comprises at least one selected from the group consisting of gold, platinum, silver, copper, aluminum, stainless steel, titanium, molybdenum, tantalum, nickel and cobalt.

7. The method for producing a balloon catheter according to claim 1, wherein
   the porous metal body is disposed on an inner part of the thermal jacket so that the porous metal body extends in an axial direction of the mold.

8. The method for producing a balloon catheter according to claim 1, wherein
   a thin film member is disposed on an inside of the porous metal body.

9. The method for producing a balloon catheter according to claim 1, wherein
   the thermal jacket includes a plurality of thermal jacket segments.

10. The method for producing a balloon catheter according to claim 1, further comprising:
    disposing the mold inside a housing member; and
    disposing the housing member inside the thermal jacket.

11. The method for producing a balloon catheter according to claim 1, wherein an amount of elastic deformation per unit thickness of the porous metal body is 3 μm/mm or more.

12. An apparatus for producing a medical resin balloon comprising:
    a mold, into which a resin tubular body is inserted, to form the medical resin balloon from the resin tubular body;
    a thermal jacket inside which the mold is disposed; and
    a porous metal body disposed outside the mold and inside the thermal jacket so that the porous metal body fills a gap that exists between the mold and the thermal jacket.

13. The apparatus for producing a medical resin balloon according to claim 12, wherein
    an amount of elastic deformation per unit thickness of the porous metal body is 3 μm/mm or more, and
    a thermal conductivity of the porous metal body is 0.325 W/m·K or more.

14. The apparatus for producing a medical resin balloon according to claim 12, wherein
an amount of initial plastic deformation per unit thickness of the porous metal body is 100 μm/mm or less.

15. The apparatus for producing a medical resin balloon according to claim 12, wherein
a metal content of material constituting the porous metal body is 90% or more.

16. The apparatus for producing a medical resin balloon according to claim 12, wherein
a number of pores per inch of the porous metal body is 8 ppi or more and 8500 ppi or less.

17. The apparatus for producing a medical resin balloon according to claim 12, wherein
the porous metal body comprises at least one selected from the group consisting of gold, platinum, silver, copper, aluminum, stainless steel, titanium, molybdenum, tantalum, nickel and cobalt.

18. The apparatus for producing a medical resin balloon according to claim 12, wherein
the porous metal body is disposed on an inner part of the thermal jacket so that the porous metal body extends in an axial direction of the mold.

19. The apparatus for producing a medical resin balloon according to claim 12, further comprising a thin film member disposed on an inside of the porous metal body.

20. The apparatus for producing a medical resin balloon according to claim 12, wherein
the thermal jacket includes a plurality of thermal jacket segments.

21. The apparatus for producing a medical resin balloon according to claim 12, wherein
a housing member is disposed inside the thermal jacket and the mold is disposed inside the housing member.

22. The apparatus for producing a medical resin balloon according to claim 12, wherein
an amount of elastic deformation per unit thickness of the porous metal body is 3 μm/mm or more.

* * * * *